US008168167B2

(12) United States Patent
Bodennec et al.

(10) Patent No.: US 8,168,167 B2
(45) Date of Patent: May 1, 2012

(54) **METHOD FOR BIOLOGICALLY COMBATING THE PROLIFERATION OF *LEGIONELLA PNEUMOPHILA*, AND NOVEL DISINFECTING AGENT CONTAINING AMOEBIC PROTOZOA OF THE *WILLAERTIA* GENUS**

(75) Inventors: Jacques Bodennec, Oullins (FR); Rafik Dey, Lyons (FR); Pierre Pernin, Lyons (FR)

(73) Assignee: Universite Claude Bernard Lyon I, Villeurbanne Cedex (FR)

( * ) Notice: Subject to any disclaimer, the term of this patent is extended or adjusted under 35 U.S.C. 154(b) by 157 days.

(21) Appl. No.: 12/311,748

(22) PCT Filed: Oct. 12, 2007

(86) PCT No.: PCT/FR2007/052131

§ 371 (c)(1),
(2), (4) Date: Dec. 31, 2009

(87) PCT Pub. No.: WO2008/043969

PCT Pub. Date: Apr. 17, 2008

(65) Prior Publication Data

US 2010/0119485 A1 May 13, 2010

(30) Foreign Application Priority Data

Oct. 12, 2006 (FR) ..................................... 06 54222

(51) Int. Cl.
*A01N 63/00* (2006.01)

(52) U.S. Cl. ..................................... 424/93.1; 424/93.4

(58) Field of Classification Search ........................ None
See application file for complete search history.

(56) References Cited

OTHER PUBLICATIONS

Ecomicth, "Etudes et retombees dans le champ", XP-002424649, Sep. 25, 2004.
Michel, R. et al., "*Legionella*-like slender rods multiplying within a strain of *Acanthamoeba* sp. isolated from drinking water", 1998, pp. 84-88, XP-002424648.
Rowbotham, T.J., "Preliminary report on the pathogenicity of *Legionella pneumophila* for freshwater and soil amoeba.", J. Clin. Pathol. 1980;33, pp. 1179-1183.
Barbaree, James M. et al., "Isolation of Protozoa from Water Associated with a *Legionellosis* Outbreak and Demonstration" Applied and Environmental Microbiology, Feb. 1986, vol. 51, No. 2, p. 422-424.
Breiman, Robert F. et al., "Association of Shower Use With Legionnaires' Disease", JAMA, Jun. 6, 1990, vol. 263, No. 21, pp. 2924-2926.
Sanden, G.N., et al., "Incubation of Water Samples Containing Amoebae Improves Detection of *Legionellae*", Applied and Environmental Microbiology, Jun. 1992, p. 2001-2004.
Steinert, Michael et al., "Resuscitation of Viable but Nonculturable *Legionella pneumophila* Philadephia JR32 by *Acanthamoeba castellanii*", A. and E. Micro., May 1997, p. 2047-2053.
Fields, Barry S., "The molecular ecology of *Legionellae*", Trends in Microbiology, vol. 4, No. 7, Jul. 1996, pp. 286-290.
Anand, C.M. et al., "Interaction of *L. pneumophila* and a free living amoeba (*Acanthamoeba palestinensis*)." J. Hyg., Camb., 1983, 91, pp. 167-178.
Holden, Edsel P. et al., "Intracellular Growth of *Legionella pneumophila* Within *Acanthamoeba castellanii* Neff", Infection and Immunity, Jul. 1984, vo. 45. No. 1 p. 18-24.
Vandenesch, F. et al., "Relationship Between Free *Amoeba* and *Legionella*: Studies in vitro and in vivo", Zbl. Bakt. 1990 vol. 272, pp. 265-275.
Moffat, Jennifer F. et al., "A Quantitative Model of Intracellular Growth of *Legionella pneumophila* in *Acanthamoeba castellanii*", Infection and Immunology, Jan. 1992, vol. 60,No. 1, pp. 296-301.
Bozue, Joel A. et al., "Interaction of *Legionella pneumophila* with *Acanthamoeba castellanii*: Uptake by Coiling Phagocytosis and Inhibition of Phasgosome-Lysosome Fusion", Infection and Immunity, Feb. 1996, vol. 64, No. 2, pp. 668-673.
Gao, Lian-Yong et al., "Utilization of Similar Mechanisms by *Legionella pneumophila* to Parasitize Two Evolutionary Distant Host Cells, Mammalian Macrophages and Protozoa", Infection and Immunity, Nov. 1997, vol. 65, No. 11, p. 4738-4746.
Neumeister, B. et al., "Multiplication of Different *Legionella* Species in Mono Mac 6 Cells and in *Acanthamoeba castellanii*", Applied and Envi. Micro., Apr. 1997, vol. 63, No. 4, p. 1219-1224.
King, C. Harold et al., "Effects of Cytochalasin D and Methylamine on Intracellular Growth of *Legionella pneumophila* in Amoebae and Human Monocyte-Like Cells", Infection and Immunity, Mar. 1991, vol. 59, No. 3, p. 758-763.
Kwaik, Yousef Abu, "The Phagosome Containing *Legionella pneumophila* within the Protozoan *Hartmannella vermiformis* Is Surrounded by the Rough Endoplasmic Reticulum", Applied and Environmental Microbiology, Jun. 1996, Vo.62, No. 6, p. 2022-2028.
Kwaik, Yousef Abu et al., "Protein Expression by the Protozoan *Hartmannella Vermiformis* upon Contact with Its Bacterial Parasite *Legionella pneumophila*", Infection and Immunity, May 1994, Vo.62, No. 5, p. 1860-1866.
Kwaik, Yousef Abu et al., "Signal Transduction in the Protozoan Host *Hartmannella vermiformis* upon Attachment and Invasion by *Legionelle micdadei*", Applied and Environmental Microbiology, Sep. 1998, Vo.64, No. 9, p. 3134-3139.
Newsome, Anthony L., "Interactions between *Naegleria fowleri* and *Legionella pneumophila*", Infection and Immunity, Nov. 1985, Vo. 50, No. 2, p. 449-452.

*Primary Examiner* — Padma Baskar
(74) *Attorney, Agent, or Firm* — Clark & Brody

(57) ABSTRACT

The invention relates to a method for biologically combating the proliferation of *Legionella pneumophila*, with the exception of the treatment methods applied to the human or animal body, characterized in that it uses amoebic protozoa of the species *Willaerita magna*, corresponding to the strain deposited with the ATCC under number PTA-7824 or the strain deposited with the ATCC under number PTA-7825.

8 Claims, 4 Drawing Sheets

METHOD FOR BIOLOGICALLY COMBATING THE PROLIFERATION OF *LEGIONELLA PNEUMOPHILA*, AND NOVEL DISINFECTING AGENT CONTAINING AMOEBIC PROTOZOA OF THE *WILLAERTIA* GENUS

The present invention relates to a method for biologically combating the proliferation of *Legionella pneumophila*, and therefore constitutes a novel method to combat the proliferation of pathogenic bacteria.

*Legionella pneumophila* is responsible in humans for legionnaires' disease and is a gram negative bacteria characterized by optional intracellular replication inside the pulmonary macrophages. Legionnaires' disease is a disease which affected 1200 people in France in 2004, causing 130 deaths. Monitoring and preventing legionnaires' disease is thus a growing concern. In addition to public health concerns, the presence of bacteria in the water of industrial plants requires strict monitoring and results in substantial exploitation losses when these installations are shut down to comply with regulations.

In the environment, *L. pneumophila* shows ubiquitous hydric distribution alongside relative thermophilia, characteristics which it shares with free amoebae. In 1980, ROWBOTHAM (ROWBOTHAM, T. J. J. Clin. Pathol. (1980) 33: 1179-1183), by analogy with what is observed in humans, was the first to hypothesise and demonstrate the existence of intracellular multiplication in *Legionella pneumophila* in protozoa cells such as free amoebae. Since then, many co-culture tests carried out in liquid media have shown considerable proliferation of *legionella* in the presence of amoebae. Other indirect arguments also reinforce the existence of interactions between free amoebae and *legionella*. Thus, during epidemics of legionnaires' disease, *legionella* and free amoebae could be isolated simultaneously from suspect waters (BARBAREE et al. Appl. Environ. Microbiol. (1986) 51: 422-424; BREIMAN et al. JAMA (1990) 263: 2924-2926). SANDEN et al. in Environ. Microbiol. (1992) 58: 2001-2004 indicate that isolating *legionella* from water is greatly improved by simple incubation of water samples in the presence of amoebae. Finally STEINERT et al. (STEINERT et al. Appl. Environ. Microbiol. (1997) 63: 2047-2053) show that the addition of amoebae is even capable of leading to revival of *legionella* strains not detectable under normal conditions since they become non-culturable in spite of remaining viable (VBNC) as a result of overly long incubation in an impoverished medium such as distilled water.

FIELDS (Trends Microbiol. (1996) 4: 286-290) counted 13 species of free amoebae and 2 ciliated species likely to lead to multiplication of *L. pneumophila*. The majority of cases of studies carried out in vitro, however, only examined 3 amoeba species: *Acanthamoeba* (ANAND et al. J. Hyg. Camb. (1983) 91: 167-178; HOLDEN et al. Neff. Infect. Immun. (1984) 45:18-24; VANDENESCH et al. Zbl. Bakt. (1990) 272: 265-275; MOFFAT et TOMPKINS Infect. Immun. (1992) 60: 296-301; BOZUE et JOHNSON, Infect. Immun. (1996) 64: 668-673; GAO et al. Infect. Immun. (1997) 65:4738-4746; NEUMEISTER et al. Appl. Environ. Microbiol. (1997) 63: 1219-1224), *Hartmannella* (KING et al. Infect. Immun. (1991) 59: 758-763; ABU KWAIK, Appl. Environ. Microbiol. (1996) 62: 2022-2028; ABU KWAIK et al. Infect. Immun. (1994) 62: 1860-1866 et Appl. Environ. Microbiol. (1998) 64: 3134-3139) and *Naegleria* (NEWSOME, Infect. Immun. (1985) 50:449-452). With these species, *legionella* multiplies in large numbers inside the amoebae where they are observed inside the phagocyte vacuoles.

Moreover, while free amoebae are suspected of assisting the preservation and multiplication of *legionella* in water-based media, notably in biofilms, no study has yet examined the repercussions on *legionella* multiplication, the complex inter-relations which can exist (competition phenomena, inter-amoeba phagocytosis) between different amoeba genera cohabiting the same amoeba microfauna.

Today, it is recognized that free amoebae play a role as carriers by means of which *legionella* develops and spreads in the environment. The techniques used at present to combat *legionella* involve thermal treatment, physical treatment (UV rays) or even chemical treatment. Nevertheless, these treatments are not entirely satisfactory as they only temporarily eliminate the planktonic bacteria of *L. pneumophila* present in a free state in the treated medium but are ineffective against bacteria that are present and protected inside protozoa.

In this context, the inventors have found, in a totally innovative manner, that certain strains of the amoeba genus *Willaertia* halt the proliferation of *L. pneumophila* bacteria and that these strains also have a phagocytic capacity towards other amoeba species likely to be infected by the bacterium.

The aim of this invention is therefore any biological prevention method using amoebae of the genus *Willaertia* against the proliferation of *Legionella pneumophila*. Methods in accordance with the invention do not include treatment methods applied to the human body or animals. In the method according to the invention, it is usually a gas or liquid flux that is treated with protozoa of the genus *Willaertia*, and in particular the species *Willaertia magna*.

The method according to the invention has particular applications in the disinfection of drinking or industrial water, cooling circuits in industrial plants or air conditioning units. In particular, the method according to the invention can be applied by adjunction of *Willaertia* amoebae to combat the proliferation of *L. pneumophila* in water pipes using biofilms, these biofilms acting as a site of development of different amoeba species. *Willaertia* amoebae can be directly added in the form of a suspension of vegetative or cystic forms to water or liquid circulating in the pipes or networks to be treated. It is also possible to envisage use of a spray, for example in the form of a suspension of cysts in evaporative cooling towers and industrial plants to be disinfected.

In particular, the biological agent used corresponds to one of two amoeba strains belonging to the species *Willaetta magna* deposited with the ATCC (American Type Culture Collection—Patent Depositary—10801 University Boulevard—Manassas, Va. 20110—United States) and registered under numbers No PTA-7824 and No PTA-7825, with a date of deposit of 21 Aug. 2006. These strains (No PTA-7824 and No PTA-7825) are an integral part of the invention and belong to the Vahlkampfiidae family. They are characterized by expression of lobular, rounded pseudopods, discharged suddenly when the amoebae move. Amoebae range in size from 45 to 100 μm in the vegetative form and from 18 to 25 μm in the cyst form. These cysts are rounded, oval in form or sometimes extremely deformed and have 7 to 12 pores in their wall. They divide by pro-mitosis.

Such amoebae, which show particularly interesting activity, can therefore be used in disinfecting agents intended especially for the elimination of *Legionella pneumophila* bacteria and to combat the spread and contamination of *legionella*.

According to another of its aspects, the invention covers a disinfecting agent containing amoebae corresponding to the strain deposited under number PTA-7824 with the ATCC or the strain deposited under number PTA-7825 with the ATCC, which are preferred. Advantageously, the disinfecting agent according to the invention is in the form of a solution or aqueous suspension, for example in distilled water. The disinfecting agent can then be used in a spray form, for example in an aerosol.

The inhibitory activity of these amoebic protozoa of the genus *Willaertia*, and in particular the species *Willaertia magna*, against *L. pneumophila* has been demonstrated by inventors by comparing replication of the bacterium in the genera *Acanthamoeba* and *Hartmannella*, used as standard amoeba models, with that of amoeba from the genus *Willaertia*. Moreover, the existence of a phagocytic process in protozoa of the genus *Willaertia* towards other amoeba genera has also been demonstrated.

Given the essential role played by free amoebae in the proliferation and preservation of *L. pneumophila* in the external environment, elements which affect the epidemiology of legionnaires' disease because there is no inter-human transmission, the method and disinfecting agent envisaged according to the invention have many advantages in terms of cost, efficacy and protection of the environment.

The examples below illustrate the invention in a non-limiting manner.

1. MATERIALS AND METHODS

1.1. Strains Used

Figure 1:
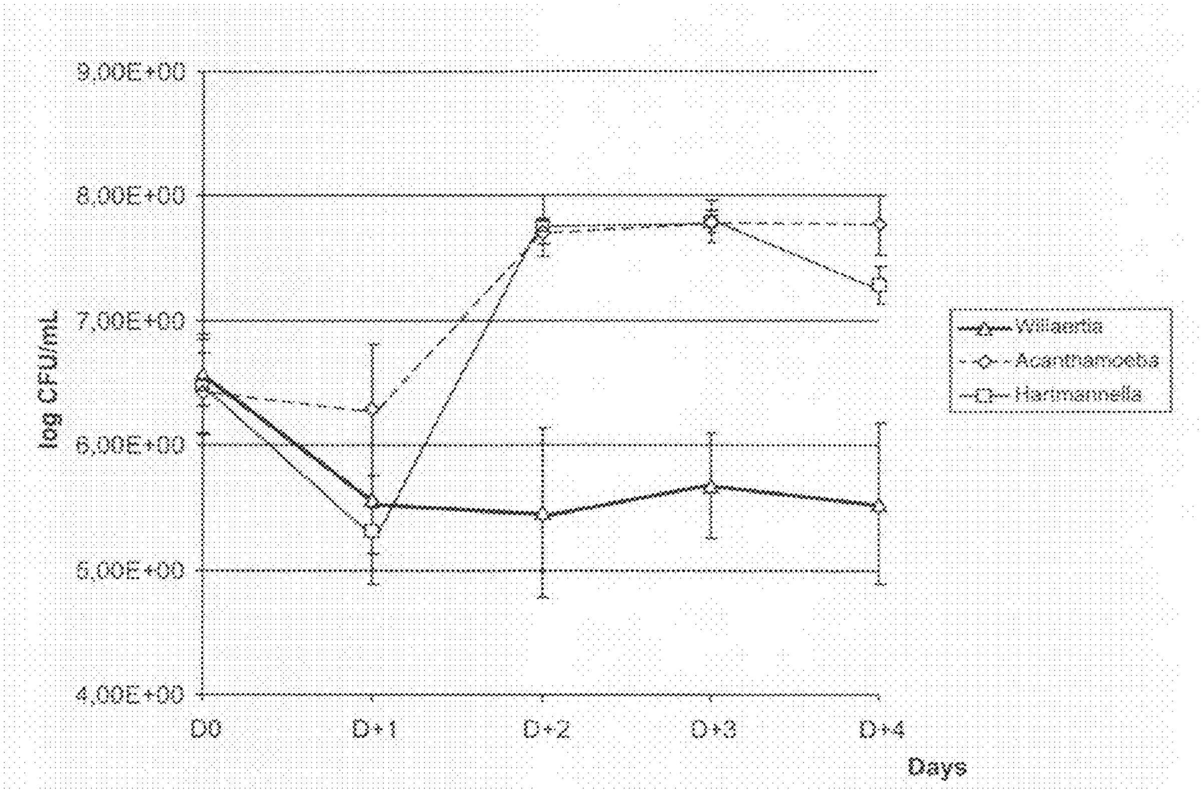
FIG. 1 shows the comparative kinetics of the development of *L. pneumophila* obtained in co-culture with different amoeba genera, including the genus *Willaertia*.

*Legionella*: The strain used is *Legionella pneumophila* serogroup 1 registered under number 107 629T at the Pasteur Institute in Paris (CNCM). It is grown on inclined BCYE agar with transplants every three weeks. The strain is seeded in broad lines on a BCYE agar plate (AES®) and incubated for three to four days at 37° C. before co-cultures are made up so as to deposit bacteria in the post-exponential phase.

Amoebae: The strains used belong to three different amoeba genera:

*Hartmannella vermiformis,*

*Acanthamoeba castellanii*

*Willaertia magna* (No PTA-7824).

These three strains are cultivated axenically in the presence of 10% foetal calf serum in SCGYEM medium (see composition in the appendix) distributed in FALCON® (3033) tubes at a rate of 3 ml per tube. In the maintenance phase, the vegetative forms are transplanted every 8-9 days. For co-cultures, 3-4 days transplants are used in such a way as to deposit trophozoites in the exponential growth phase.

SCGYEM medium

Composition:

| | | |
|---|---|---|
| Casein (MERCK 1.02244.010) | 10 | g |
| $Na_2HPO_4$ | 1.325 | g |
| $KH_2PO_4$ | 0.8 | g |
| Glucose | 2.5 | g |
| Yeast extract (DIFCO 0127-17-9) | 5 | g |
| Distilled water | 900 | ml |
| Foetal calf serum | 100 | ml |

2.5 ml NaOH (1N), then $Na_2HPO_4$ and $KH_2PO_4$ are added to 900 ml of distilled water. This is heated gently on a hotplate, then casein is gradually added under magnetic stirring. After the casein dissolves, glucose and yeast extract are added.

After complete dissolution, the mixture is filtered successively on fibreglass (SARTORIUS SM 6513400), then on a 1 μm membrane (WHATMAN 7190 004). Aliquots of the medium are then placed in glass bottles. The bottles are sterilized in the autoclave for 20 minutes at 120° C. Before final use and distribution of the medium, foetal calf serum is added under sterile conditions at a concentration of 10% of the final volume in a laminar flow closet.

1.2. *L. pneumophila* Monoamoeba Co-Culture 1.2.1. Preparation of the Bacterial Inoculum:

Using the 3-4 day culture on BCYE agar, a suspension of *L. pneumophila* is prepared in sterile distilled water so as to obtain 1 optic density unit at 550 nm, i.e. a concentration of $10^9$ UFC/ml.

1.2.2. Production of Mono-Amoeba Co-Cultures

The co-cultures are made up in cell culture tubes (FALCON® 3033) containing 3 ml of SCGYEM medium. Tube seeding is carried out at a rate of about $7\cdot10^4$ amoebae/ml using an axenic amoeba suspension previously counted on a THOMA cell. Amoeba infection by *L. pneumophila* is carried out at an *L. pneumophila*/amoeba ratio of 50, that is about 3.5 $10^6$ bacteria/ml. Immediately after infestation, the co-culture tubes are centrifuged at low speed (760 g for 5 min) to promote contact between amoebae and bacteria. After 10 mins, the tubes are manually re-suspended and incubated in an inclined position in the oven at 37° C.

1.2.2.1 Kinetic Study of Co-Cultures

Co-cultures are observed for at least 5 days (D0 to D+4) after bacterial infestation. At each time interval, a tube is removed and examined both for amoebae and bacteria after vigorous stirring in a vortex in order to detach amoebae from the walls. For each tube examined:

Amoebae are counted directly on a THOMA or MALASSEZ cell.

In view of the results obtained following preliminary amoeba lysis tests, total *legionella* numbers were counted by direct distribution on a BCYE agar medium (AES° after 10 in 10 dilution in sterile distilled water in Eppendorf tubes. Each dilution is carried out in triplicate on BCYE agar at a rate of 100 μl per plate. Plates are then incubated at 37° C. for a minimum of 6 days. A first reading is performed from the $4^{th}$ day of the colony count. This is followed by a second reading on the $6^{th}$ day for confirmation. The number of *L. pneumophila* is expressed in UFC/ml taking into account the dilution factor and assuming that each colony corresponds to 1 bacterium initially present in the diluted suspension.

For each amoeba genus, the growth graphs for *L. pneumophila* are represented as a function of time and correspond to the mean of at least three independent tests with the corresponding standard deviations.

Given the slowness of *L. pneumophila* colony growth in BCYE cultures, the results for tests of this type take at least 11 days.

1.2.2.2 Cytotoxicity of *L. pneumophila* for Other Amoeba Genera

Co-cultures of three amoeba genera were also made up in 24-well microplates containing $5 \cdot 10^4$ amoebae/well infested at an *L. pneumophila*/amoeba ratio of 50 in order to microscopically observe cell monolayers and provide a qualitative evaluation of the cyptopathogenic effect of the bacterium against amoeba.

Cytotoxicity was also determined after 48 and 72 hours co-culture using the Trypan Blue exclusion test on the genera *Acanthamoeba* and *Willaertia*. The amoebae are recovered by gentle centrifugation of co-culture tube contents, then resuspended in 200 µl of SCGYEM medium prior to mixing with Trypan Blue in a ratio of 4/1. Cells are examined on a hematimeter and the percentage of killed cells, which turn blue, is determined for each amoeba genus.

1.3. *L. pneumophila* Tripartite Co-Cultures

The possible repercussions of interactions between different amoeba genera, notably of inter-amoeba phagocytosis, on *legionella* replication and transmission was studied. Initially, the kinetics of the inter-amoeba phagocytosis process between *Hartmannella* and *Willaertia* were studied then tripartite co-cultures of *L. pneumophila* involving two amoeba hosts were carried out.

1.3.1. Study of the Inter-Amoeba Kinetics of Phagocytosis of *Hartmannella*-*Willaertia*

Using respective axenic co-cultures, a series of SCGYEM tubes containing both *Hartmannella* amoebae and *Willaertia* is prepared in a fixed ratio of around 20 *Hartmannella* per 1 *Willaertia*. The phagocytic process is observed in vivo under a phase contrast microscope and, as a result of marked differences in size and appearance between the two amoeba genera, the progress was tracked by counting the two amoeba populations present at different time intervals.

1.3.2. Production of *L. pneumophila* Tripartite Co-Cultures

A two-step experimental protocol was used to make up these co-cultures:

- the first step corresponds, as for the monoamoeba co-cultures, to infestation in a co-culture of the first amoeba host by *L. pneumophila.*
- the second step consists in introducing a second amoeba genus into the co-culture after elimination of extracellular *legionella.*

1.3.2.1. Infestation of the First Amoeba Host on D−1:

This step corresponds to infestation of the amoeba *H. vermiformis* with *L. pneumophila*. It is carried out in FALCON tubes under conditions similar to those described in paragraph 1.2.2. The only differences concern the initial amoeba concentration which is in the order of $2 \cdot 10^5$ *Hartmannella*/ml and the *L. pneumophila/Hartmannella* infestation ratio which is 20. The tubes are incubated in an inclined position for 24 H at 37° C.

1.3.2.2. Addition of the Second Amoeba Host on D0

✎Elimination of Extracellular Legionellas

At the end of the incubation time to infest the first amoeba host, extracellular *legionella* was eliminated by treatment of co-cultures with gentamycin at a concentration of 50 µg/ml for 1H at 37° C. (Moffat, J. F, and Tompkins, L. S. Immun. (1992) 60: 296-301). After centrifugation at 2000 g for 10 min, the antibiotic is eliminated by decantation of the culture medium and the *Hartmannella* cellular residue is washed twice with 2 ml of serum-free SCGYEM medium to eliminate all traces of the antibiotic. After the final washing, the amoeba residue in each tube was resuspended by placing in a vortex in its initial volume of SCGYEM medium (3 ml). Counting (D0) of both *Hartmannella* and *legionella* is carried out.

✎Inoculation of the Second Amoeba Host (*Willaertia*)

In parallel, an amoeba suspension of the second host *Willaertia* was made up using an axenic culture. After counting in a THOMA cell, the necessary volume of suspension to be added to the co-culture tubes constituting the "test" series is calculated to obtain a $1^{st}$ amoeba host/$2^{nd}$ amoeba host (*Hartmannella/Willaertia*) cell ratio of about 20. The tubes corresponding to the "control" series are treated in exactly the same way but no *Willaertia* amoebae are added after treatment with gentamycin.

✎Follow-Up of Co-Cultures D0 to D+5

Each day, after stirring in a vortex, one co-culture tube from the "test" and "control" series is examined for amoebae and bacteria:

- The trophozoite count for each amoeba genus is carried out on a THOMA or MALASSEZ cell.
- Total *legionella* counts are carried out, as in the case of monocultures, by applying dilutions of the culture medium in sterile distilled water on BCYE agar. A single manipulation therefore takes 12 or so days for interpretation.

2. RESULTS

2.1. Results of Monoamoeba Co-Cultures of *L. pneumophila.*

◈Absence of *L. pneumophila* Growth in the Presence of *Willaertia* Amoebae

FIG. 1 shows the comparative growth of *L. pneumophila* in co-culture with three amoeba genera, the co-cultures being carried out as described previously in the materials and methods section, in other words axenic amoebae on SCGYEM medium are co-cultured in the presence of *L. pneumophila* from D0 in an *L. pneumophila*/amoeba ratio of 50. The results correspond to the mean±standard deviation of 6 (*Hartmannella*) to 8 (*Acanthamoeba* and *Willaertia*) independent tests.

*L. pneumophila* co-cultures made up in the presence of amoebae from the genus *Hartmannella* and genus *Acanthamoeba* confirm the overall multiplication of bacteria in the presence of the two amoeba genera because an increase of up to 1.3 and 1.4 log is observed at D+3 (FIG. 1), respectively. Conversely, although the experimental conditions are strictly identical, *L. pneumophila* co-cultures in the presence of *Willaertia* sp. amoebae not only do not lead to significant bacterial development but lead to a 1 log reduction in the bacterial population. Eventually, the difference in the development of *L. pneumophila* between the co-cultures in the presence of *Hartmannella* sp. and *Acanthamoeba* sp. and the co-cultures in the presence of *Willaertia* sp. amoebae reaches 2.3 log at D+2 (FIG. 1).

Simultaneously, observation under the microscope of co-cultures shows substantial morphological modifications affecting only amoebae of the genus *Hartmannella* and *Acanthamoeba*. Their trophozoites become gradually rounded and shrivelled and lose their adherence capacity from D2 to D4. Under these conditions, the precise amoeba count for these two genera becomes difficult and uncertain since the majority of cells counted are already necrotic and on the verge of lysis. Nevertheless, the count shows that the growth of these two genera slows down as of D+1 with a clear decrease from D+2 (Table 1). The co-cultures in the presence of *Willaertia* sp. do not show this involution and, to the contrary, are characterized by amoebic proliferation (Table 1).

The results presented in Table 1 are obtained as follows:

Different amoeba species were co-cultured in the presence of *L. pneumophila* in an infestation ratio of 50 (*L. pneumophila*/amoeba) and the amoebae are counted on a daily basis on a hematimeter. The number of amoebae/ml of medium results correspond to the mean of 6 (*Hartmannella*) to 8 (*Acanthamoeba* and *Willaertia*) independent experiments. The statistically significant differences between the number of *Willaertia* and the other two amoeba species are given (*: P<0.05; **: P<0.001).

TABLE 1

Effect of bacterial infection on *amoeba* growth

| *Amoeba* species | Time (co-culture day) 0 | 1 | 2 | 3 |
|---|---|---|---|---|
| *Acanthamoeba castellanii* | $5.38\ 10^4$ ± $3.86\ 10^3$ | $1.35\ 10^5$ ± $5.91\ 10^4$ | $1.13\ 10^5$ ± $5.67\ 10^4$ ** | $3.64\ 10^4$ ± $3.05\ 10^4$ ** |
| *Hartmannella vermiformis* | $5.50\ 10^4$ ± $4.60\ 10^3$ | $1.97\ 10^5$ ± $4.63\ 10^4$ | $2.32\ 10^5$ ± $3.76\ 10^4$ * | $1.26\ 10^5$ ± $2.96\ 10^4$ ** |
| *Willaertia magna* | $5.41\ 10^4$ ± $2.52\ 10^3$ | $1.77\ 10^5$ ± $3.93\ 10^4$ | $2.92\ 10^5$ ± $5.26\ 10^4$ | $2.42\ 10^5$ ± $4.71\ 10^4$ |

◈Absence of *L. pneumophila* Cytotoxicity Towards *Willaerita* Amoebae

Figure 2:
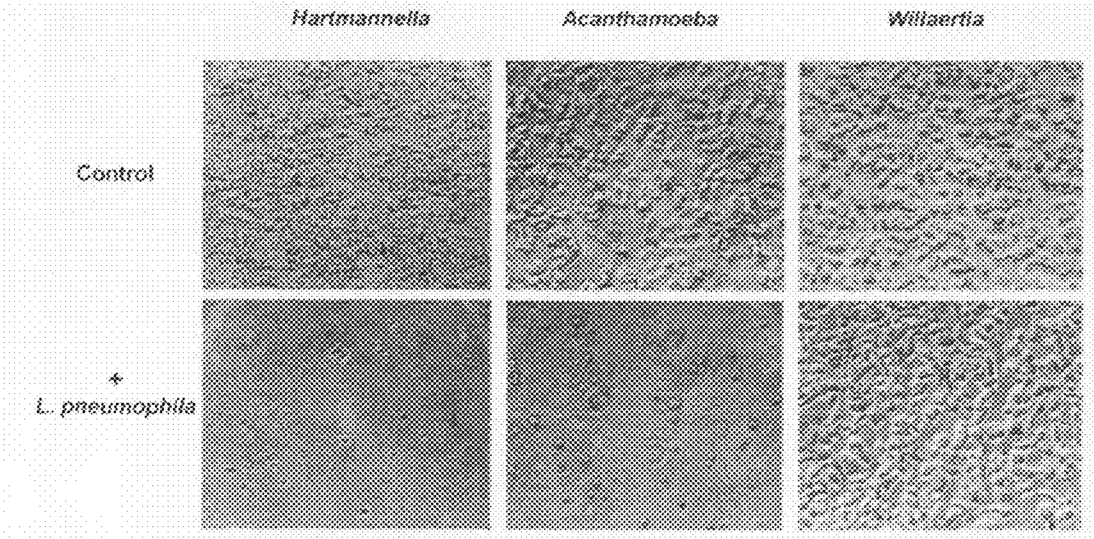
FIG. 2 shows the effect of *L. pneumophila* on different amoeba species and the particular resistance of *Willaertia* with respect to *Hartmannella* and *Acanthamoeba*.
Figure 3:
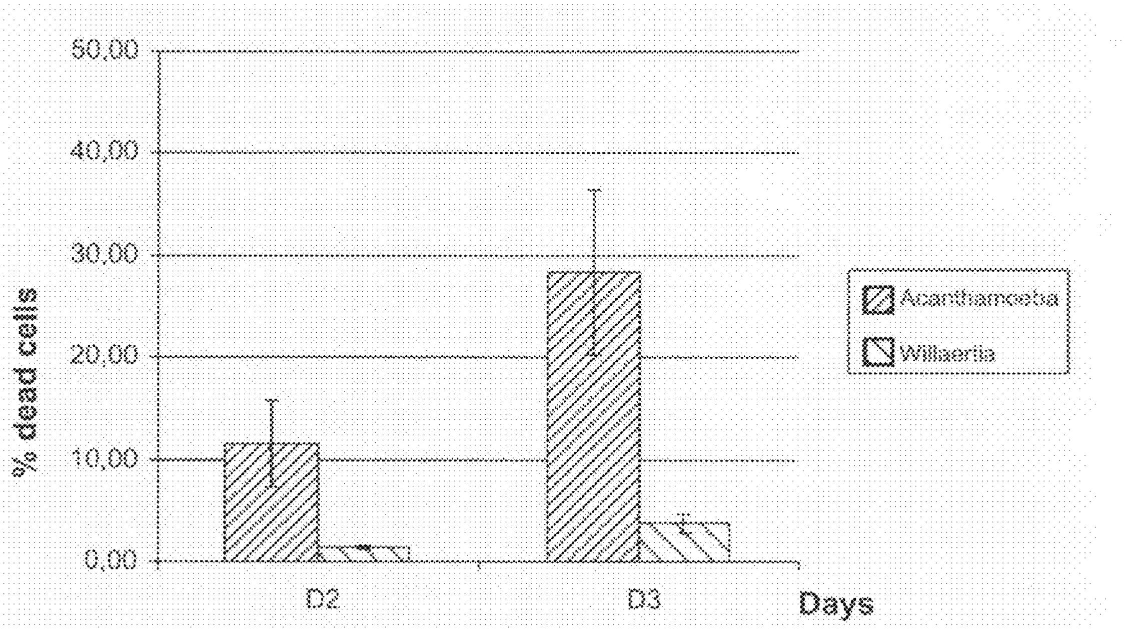
FIG. 3 shows the resistance of *Willaertia* against cytotoxicity caused by *L. pneumophila*. However, it should be noted that there is a pronounced cytotoxic effect with *Acanthamoeba*.

The cytotoxic effect of *L. pneumophila* for amoebae was examined by phase contrast microscope observation of co-cultures in microplates. FIG. 2 shows the images obtained by phase contrast microscopy for various amoeba species cultured in the absence (top) and presence (bottom) of *L. pneumophila* for 72 H at an infestation ratio of 50. Under these conditions, it is found that *L. pneumophila* completely destroys monolayers of the *Hartmannella* sp. and *Acanthamoeba* sp. strains after 72 H of infection with the appearance of detached and rounded cells (FIG. 2) whereas for the same infestation ratio and the same time period, *Willaertia* sp. monolayers remain intact and proliferate equally well in the control wells devoid of *legionella* (FIG. 2). These observations were confirmed by carrying out a Trypan Blue exclusion test on co-cultures of *Acanthamoeba* and *Willaertia*. FIG. 3 illustrates the comparative cytotoxicity of *L. pneumophila* for *Acanthamoeba* and *Willaertia*. Amoebae are cultured in the presence of *L. pneumophila* and the percentage of Trypan Blue positive cells after 2 to 3 days in co-cultures was determined microscopically. The data presented in FIG. 3 correspond to the results obtained from 5 separate tests.

The results show that 28.4±8% of the rare *Acanthamoeba* sp. cells still present after 72 H are killed. On the other hand, the cytopathogenic effect of *L. pneumophila* on *Willaertia* sp. is less than 4% after the same infection time (FIG. 3). Thus morphologically, *Willaertia* trophozoites in co-culture appear to be more resistant to infection by *L. pneumophila* than *Hartmannella* or *Acanthamoeba* trophozoites.

2.2. Kinetics of the Inter-Amoeba Phagocytosis Process

Phagocytosis of *Hartmannella* amoebae by *Willaertia* amoebae begins in the minutes following contact between the two amoeba genera. The phenomenon is triggered by random encounters between the two amoeba genera and its evolution therefore depends on the respective proportions of the two genera in contact.

Figure 4:
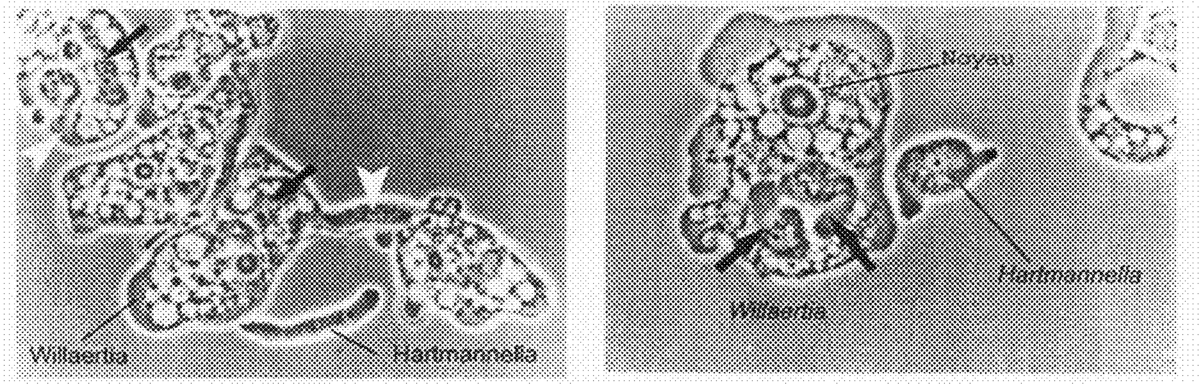
FIG. 4 shows live phagocytosis of *Hartmannella* amoebae by *Willaertia* amoebae observed under phase contrast microscopy (×1200).

Microscopically, it is perfectly possible to follow the in vivo ingestion of *Hartmannella* by *Willaertia* and it is not unusual to observe a *Willaertia* cell containing several *Hartmannella* trophozoites at a more or less advanced stage of digestion as illustrated in FIG. 4. FIG. 4 which represents phase contrast microscopy views (×1200) shows the phagocytosis of *Hartmannella* amoebae by *Willaertia* amoebae observed in vivo. The black arrows indicate the presence of *Hartmannella* trophozoites phagocytosed inside the cytoplasm of *Willaertia* amoebae. The white dot indicates a *Hartmannella* amoeba that is simultaneously prey to two *Willaertia* amoebae.

Figure 5:
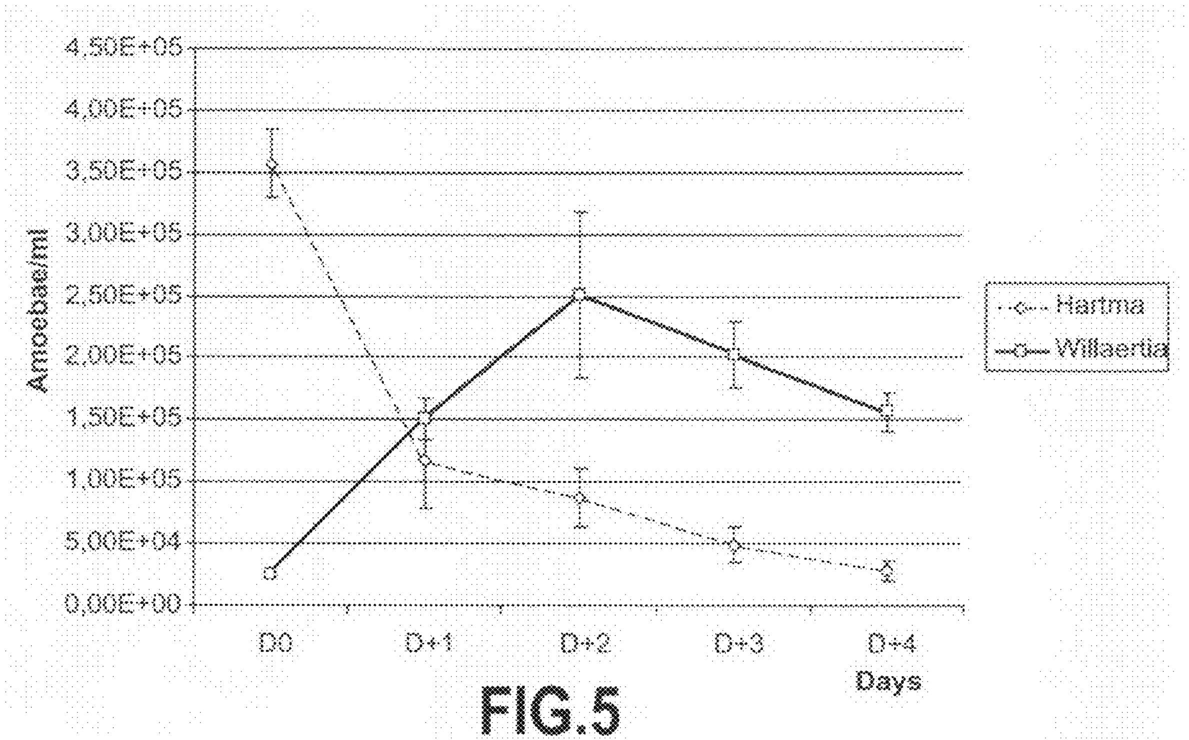
FIG. 5 shows the spontaneous evolution of respective populations of *Hartmannella* (H) and *Willaertia* (W) amoebae after their contact in an initial H/W ratio of about 15.

The kinetic study of this phenomenon shows that after this phagocytic process, there is a very rapid decrease in the *Hartmannella* population which drops to 14% of its initial value in 3 days whereas the *Willaertia* simultaneously increases by 1 log in 2 days. There is a complete reversal of the H/W ratio which drops from 14.4 to 0.24 between D0 and D+3. (FIG. 5 shows the respective development of *Hartmannella* (H) and *Willaertia* (W) populations in mixed axenic cultures in an H/W ratio of 15.)

2.3. Results of Tripartite Co-Cultures (Bi-Amoebic) of *L. pneumophila*.

Figure 6:
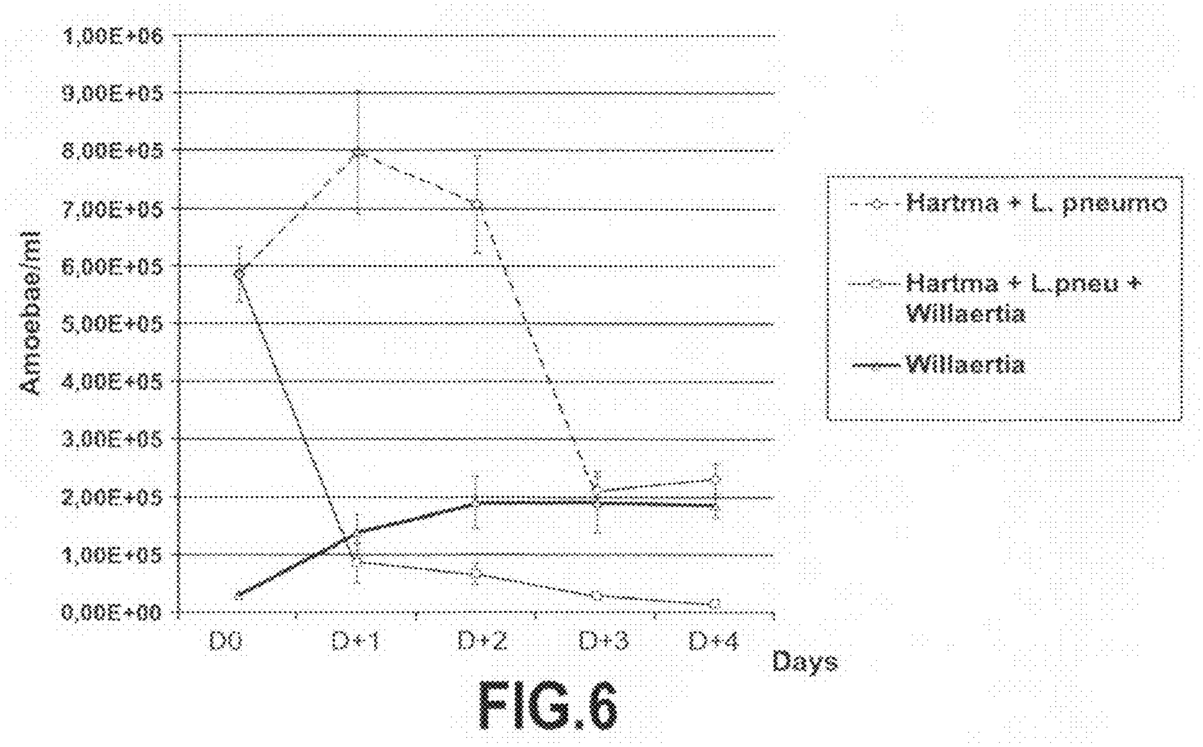
FIG. 6 represents the respective development of *Hartmannella* amoeba populations ("control" and "test" series) and *Willaertia* amoebae in *L. pneumophila* co-cultures.
Figure 7:
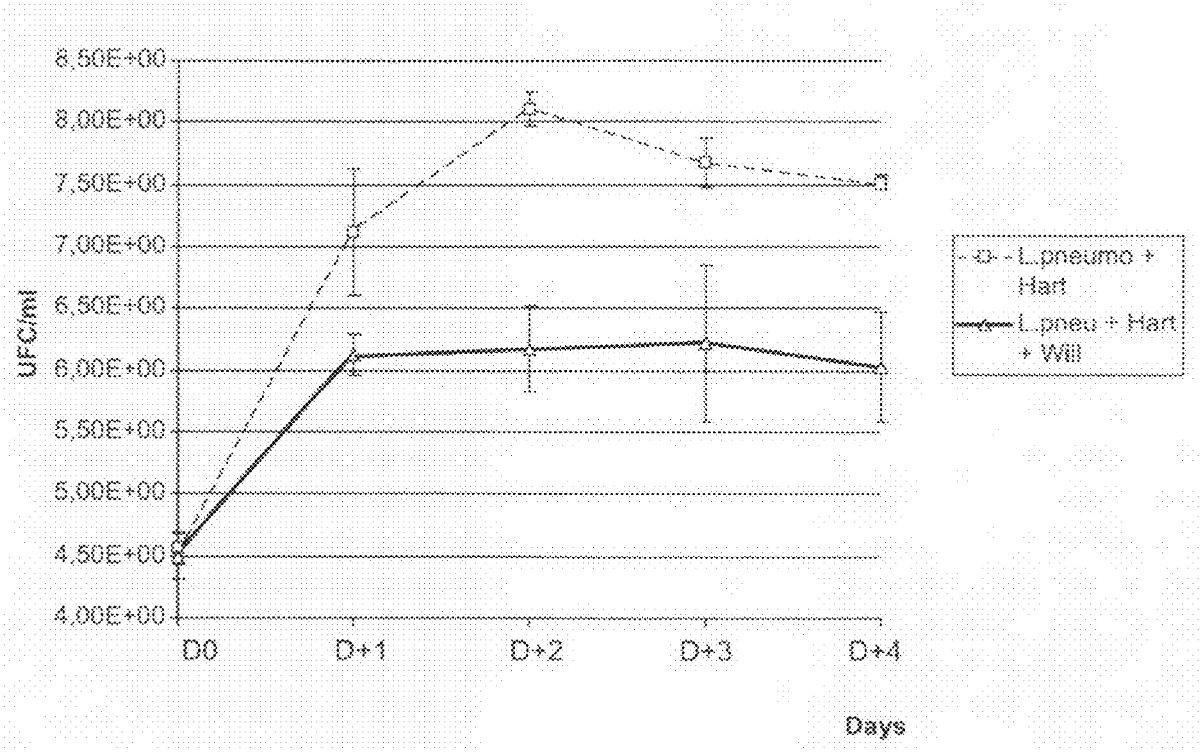
FIG. 7 represents the comparative kinetics of the development of *L. pneumophila* in monoamoeba co-culture (*Hartmannella* alone) and in tripartite co-cultures (*Hartmannella*+*Willaertia*).

The introduction of the amoeba *Willaertia* in tripartite co-cultures from D0, in other words 24 H after infestation of the first amoeba host *Hartmannella* by *L. pneumophila*, is accompanied by two concomitant phenomena and confirms the previously observed effect found in mono-amoeba co-cultures:

1. FIG. 6 shows the respective growth of amoeba species in the presence of *L. pneumophila* as a function of the previously described co-culture conditions in the materials and method section, that is amoebae of the genus *Hartmannella* which underwent preliminary infection on D−1 for 2 H with *L. pneumophila* in an infestation ratio of 20. At D0, after elimination of extracellular *legionella* by treatment with Gentamycin (1H) and thorough washing, pre-infected *Hartmannella* (H) amoebae were re-suspended in their initial volume in SCGYEM medium and received amoebae of the genus *Willaertia* (W) in the "test" series in an H/W ratio of 20 (tripartite co-culture). The "control" series develops in the absence of *Willaertia* and corresponds to a monoamoeba co-culture. The amoeba populations are counted each day in each of the "control" and "test" series. Logically, there is a faster decrease in *Hartmannella* amoebae in the "test" series, reaching up to 86% in the first 24 H after the inter-amoeba phagocytic process is triggered, than in the "control" series where the disappearance of *Hartmannella* is due to necrotic lysis caused by *L. pneumophila* (FIG. 6). In parallel, there is a constant increase in *Willaertia* whose numbers are multiplied by 6.5 during the experiment and as previously the H/W ratio is completely reversed, decreasing from 19.8 to 0.08. As already seen with the monoamoeba co-cultures, the presence of *legionella* does not therefore appear to affect the morphological appearance of the development of *Willaertia.*
2. FIG. 7 shows the comparative increase in *L. pneumophila* in monoamoeba co-culture with *Hartmannella* alone and in tripartite co-culture in the presence of *Hartmannella* and *Willaertia* added from D0. The operating method is that described previously in FIG. 6. The development of *L. pneumophila* stops compared to the growth found in the "control" co-cultures in the presence of *Hartmannella* amoebae only (FIG. 7). Inhibition of *L. pneumophila* development following addition of *Willaertia* reaches 2 log after 48 H in tripartite co-culture. Visibly therefore the *Hartmannella* phagocytosis process by *Willaertia* does not relay and amplify bacterial replication in the new host.

In conclusion, the tendency observed during monoamoeba co-cultures of *L. pneumophila* with *Willaertia* is amply confirmed by the results of tripartite co-cultures. It is noted that phagocytosis by *Willaertia* of the first amoeba host, previously infested for 24 H, completely blocks the development of *legionella* compared to the changes observed in *Hartmannella* control co-cultures without *Willaertia*. Visibly the increase in the *Willaertia* population and the accompanying phagocytic process do not allow transmission of infestation from the first cell host to a potential second host. The relative stability of *legionella* levels at values close to the starting values can be maintained by *Hartmannella* yet to be phagocytosed. This set of results shows the absence of *L. pneumophila* development in the presence of amoebae of the genus *Willaertia*.

Results which accord with the set of results obtained above with strain No PTA-7824 are also obtained with strain No PTA-7825.

The invention claimed is:

1. A method for biologically combating the proliferation of *Legionella pneumophila*, with the exception of the treatment methods applied to the human or animal body, comprising contacting amoebic protozoa of the species *Willaertia magna*, corresponding to the strain deposited with the ATCC under number PTA-7824 or the strain deposited with the ATCC under number PTA-7825 with *Legionella pneumophila* for combating proliferation thereof.

2. The method according to claim 1 characterised in that it is applied to the treatment of a liquid or gas flux using amoebic protozoa.

3. The method according to claim 1 characterised in that it is applied for the disinfection of drinking or industrial water distribution networks, cooling circuits and evaporative cooling towers in industrial plants or air conditioning units.

4. The method according to claim 1 characterised in that it is applied to combat the proliferation of *L. pneumophila* in water pipes using biofilms.

5. The method according to claim 2 characterised in that it is applied for the disinfection of drinking or industrial water distribution networks, cooling circuits and evaporative cooling towers in industrial plants or air conditioning units.

6. The method according to claim 2 characterised in that it is applied to combat the proliferation of *L. pneumophila* in water pipes using biofilms.

7. A disinfecting agent containing amoebic protozoa of the species *Willaertia magna*, corresponding to the strain deposited under number PTA-7824 with the ATCC or the strain deposited under number PTA-7825 with the ATCC.

8. The disinfecting agent according to claim 7 characterised in that it is in the form of a solution or of an aqueous suspension.

* * * * *